United States Patent [19]

Li Bassi et al.

[11] Patent Number: 4,987,159

[45] Date of Patent: Jan. 22, 1991

[54] CARBONYL DERIVATIVES OF 1-PHENYLINDAN SUITABLE FOR USE AS POLYMERIZATION PHOTOINITIATORS, THEIR PREPARATION AND USE

[75] Inventors: Giuseppe Li Bassi, Gavirate; Carlo Nicora, Varese; Fabrizio Broggi, Buguggiate; Aldo Revelli, Cittiglio, all of Italy

[73] Assignee: Fratelli Lamberti S.p.A., Albizzate, Italy

[21] Appl. No.: 507,452

[22] Filed: Apr. 11, 1990

[51] Int. Cl.$^5$ .......................... C07C 49/00; C08F 2/50
[52] U.S. Cl. ...................... 522/36; 568/327; 522/96; 522/85; 204/157.15
[58] Field of Search .................. 522/36; 568/323, 327; 204/157.15

[56] References Cited

U.S. PATENT DOCUMENTS

| | | | |
|---|---|---|---|
| 2,448,828 | 9/1948 | Renfrew | 522/13 |
| 3,340,233 | 9/1967 | Leavitt | 526/284 |
| 3,715,293 | 2/1973 | Sandner et al. | 522/44 |
| 4,318,791 | 3/1982 | Felder et al. | 522/33 |
| 4,347,111 | 8/1982 | Gehlhaus et al. | 522/8 |

Primary Examiner—John F. Niebling
Assistant Examiner—Isabelle R. McAndrews
Attorney, Agent, or Firm—Birch, Stewart, Kolasch & Birch

[57] ABSTRACT

New carbonyl derivatives of 1-phenylindan suitable for use as photoinitiators in the photopolymerization of compounds or mixtures of compounds containing ethylenic double bonds.

The carbonyl derivatives of 1-phenylindan according to the present invention possess high efficiency as photoinitiators in terms both of the concentration used and the photopolymerization rate.

14 Claims, No Drawings

CARBONYL DERIVATIVES OF 1-PHENYLINDAN SUITABLE FOR USE AS POLYMERIZATION PHOTOINITIATORS, THEIR PREPARATION AND USE

This invention relates to new carbonyl derivatives of 1-phenylindan suitable for use as photoinitiators for the photopolymerisation of compounds or compound mixtures containing ethylenic double bonds.

More specifically, the invention relates to new carbonyl derivatives of 1-phenylindan, their production process and their use in photopolymerisable mixtures.

The photochemical polymerisation of unsaturated monomers and prepolymers is a well known process which has wide industrial application.

This type of reaction occurs by the interaction of light energy, within a precisely defined portion of the electromagnetic spectrum, and a suitable substrate able to absorb the light and undergo polymerisation. By various mechanisms depending on the nature of the substances present, the irradiation results in the generation of radical species which within a very short time give rise to polymerisation of the molecules containing ethylenic double bonds. To aid light absorption and the generation of the radical species, photosensitisers and photoinitiators are generally used.

Photosensitisers serve to absorb and transfer light energy whenever the photoinitiator does not absorb in the spectral regions useful for the photochemical reaction, whereas photoinitiators serve to generate the radicals which promote polymerisation.

The efficiency of these products has been gradually improved as the industries employing photopolymerisation processes have become more widespread, these including paints and lacquers, printing inks, the manufacture of printing plates and electronic circuits, silk screens for ceramic and textile printing, transfer printing, and dentistry use.

The term "efficiency" when applied to these products relates in particular to their reactivity, in terms both of their quantum yield (quantity of monomer converted for each quantum of light absorbed) and the polymerisation rate, but also to the stability of mixtures containing the photoinitiator under dark conditions.

THE TECHNICAL PROBLEM

Notwithstanding the great progress made in this sector during recent years with the introduction of many photoinitiators, there is continuous research directed towards the discovery of substances which are ever more active, more dark-stable, less easily separated from the mixtures to be polymerised and which do not leave indesirable residues, e.g. which do not give rise to undesirable colouring or odour in the polymerised substance.

PRIOR ART

As stated heretofore, many substances have been used as photoinitiators, such as benzoin alkyl ethers described in U.S. Pat. No. 2,448,828, dialkoxyacetylphenones and benzylmonoketals described in U.S. Pat. No. 3,715,293, or benzophenone in combination with hydrogen donors of tertiary amine type.

More recently, certain products of the substituted acetophenone class have been introduced, such as those proposed in U.S. Pat. Nos. 4,318,791 and 4,347,111.

In particular in the case of acrylic systems, 2,2-dialkyl-2-hydroxyacetophenones have enabled problems connected with the yellowing of the photo-crosslinked product (because of the U.V. light of the crosslinking lamp and subsequent ageing by exposure to natural light) to be solved without this resulting in decreased efficiency.

The present applicant in European patent application No. 161463 describes a class of aromatic-aliphatic ketones with excellent photoinitiator properties.

DETAILED DESCRIPTION OF THE INVENTION

According to a basic characteristic of the present invention, 1-phenylindan carbonyl derivatives with high photoinitiator activity in the polymerisation of compounds or compound mixtures containing ethylenic double bonds have the following general formula:

where:

n: ranges from 0 to 1

R, $R^1$, $R^2$: which can be identical or different, each independently represent H, $C_1$–$C_3$ alkyl Q: represents a $$-\overset{O}{\underset{\phantom{|}}{C}}-\overset{R^3}{\underset{R^4}{C}}-X$$

group in which $R^3$, $R^4$, which can be identical or different can each independently represent:

$C_1$–$C_8$ alkyl together can represent a $C_3$–$C_7$ polyalkylene group together can be coincident in an oxygen atom X: can be Cl, OH, OR in which R has the aforesaid meaning.

The compounds according to the invention have high efficiency in terms both of the concentration in which they are used and the polymerisation rate; they have excellent resistance to ageing on exposing the resultant manufactured articles to light; they have a total absence of odour both during polymerisation and during the subsequent life of the manufactured article; and they have low volatility and total compatibility with the photopolymerisable products with which they are mixed, both as the product itself and as the residue after polymerisation. This latter characteristic means that the migration of the photoinitiator or of its residues is practically zero within the manufactured article, with no consequent undesirable effects.

The characteristics of the products according to the invention suggest their use in the photoinitiated polymerisation and free radical crosslinking of compounds or compound mixtures containing ethylenic double bonds.

These compounds can be monomers, oligomers or polymers.

Particularly suitable monomers include:
acrylic and methacrylic acid derivatives (esters, amides, salts, the acids themselves, nitriles)
N-vinylpyrrolidone
vinyl esters
styrene
allyl derivatives For oligomers and polymers the preferred compounds are those with acrylic or methacrylic unsaturations in chains of the following types:
polyester
polyether
polyurethane
silicone
epoxide
or with maleic, fumaric or allyl unsaturations in polyester chains.

The compounds according to the invention are particularly useful in the polymerisation of compositions containing compounds or compound mixtures of acrylic and/or methacrylic type.

Preferred uses include:
paints and inks in which high reactivity is required together with a low level of yellowing both immediately and after exposure to light sources, and by ageing under light (such as paints in paper technology and for plastics materials);
paints, inks and adhesives in which residual odour after photo-crosslinking should be limited to the minimum possible (graphic art materials);
paints and inks in which in order to properly exercise its activity, the photoinitiator must not be volatile (emulsions for which the aqueous phase must be removed before photo-crosslinking);
photopolymerised masses in which all these requirements exist (photo-crosslinkable masses for dentistry use and for manufacturing printing plates).

The preferred carbonyl derivatives of 1-phenylindan according to the invention for use as photoinitiators include the alphaketoester, halo-ketone and hydroxy-ketone derivatives, and in particular;

2,3-dihydro-5-(2-methyl-1-oxopropyl)-1,1,3-trimethyl-3-[4-(2-methyl-1-oxopropyl)phenyl]-1H-indene in mixture with
2,3-dihydro-6-(2-methyl-1-oxopropyl)-1,1,3-trimethyl-3-[4-(2-methyl-1-oxopropyl)phenyl]-1H-indene;
2,3-dihydro-5-(2-chloro-2-methyl-1-oxopropyl)-1,1,3-trimethyl-3-[4-(2-chloro-2-methyl-1-oxopropyl)phenyl]-1H-indene in mixture with
2,3-dihydro-6-(2-chloro-2-methyl-1-oxopropyl)-1,1,3-trimethyl-3-[4-(2-chloro-2-methyl-1-oxopropyl)phenyl]-1H-indene;
2,3-dihydro-5-(2-hydroxy-2-methyl-1-oxopropyl)-1,1,3-trimethyl-3-[4-(2-hydroxy-2-methyl-1-oxopropyl)phenyl]-1H-indene in mixture with
2,3-dihydro-6-(2-hydroxy-2-methyl-1-oxopropyl)-1,1,3-trimethyl-3-[4-(2-hydroxy-2-methyl-1-oxopropyl)phenyl]-1H-indene;
2,3-dihydro-5-(2-hydroxy-2-methyl-1-oxopropyl)-1,1,3-trimethyl-3-[4-(2-hydroxy-2-methyl-1-oxopropyl)phenyl]-1H-indene;
2,3-dihydro-6-(2-hydroxy-2-methyl-1-oxopropyl)-1,1,3-trimethyl-3-[4-(2-hydroxy-2-methyl-1-oxopropyl)phenyl]-1H-indene;
2,3-dihydro-5-(2-ethoxy-1,2-dioxoethyl)-1,1,3-trimethyl-3-[4-(2-ethoxy-1,2-dioxoethyl)phenyl]-1H-indene in mixture with
2,3-dihydro-6-(2-ethoxy-1,2-dioxoethyl)-1,1,3-trimethyl-3-[4-(2-ethoxy-1,2-dioxoethyl)phenyl]-1H-indene;
2,3-dihydro-1,3-dimethyl-5-(2-hydroxy-2-methyl-1-oxopropyl)-1-{2-methyl-2-[4-(2-hydroxy-2-methyl-1-oxopropyl)phenyl]propyl}-3-[4-(2-hydroxy-2-methyl-1-oxopropyl)phenyl]-1H-indene in mixture with
2,3-dihydro-1,3-dimethyl-6-(2-hydroxy-2-methyl-1-oxopropyl)-1-{2-methyl-2-[4-(2-hydroxy-2-methyl-1-oxopropyl)phenyl]propyl}-3-[4-(2-hydroxy-2-methyl-1-oxopropyl)phenyl]-1H-indene.

According to one characteristic of the invention, photopolymerisable compositions comprising compounds with olefinic double bonds are prepared by incorporating therein a quantity of one compound of formula (I), or a mixture of more than one compound thereof, of between 0.1 and 10 parts by weight per 100 parts of composition:

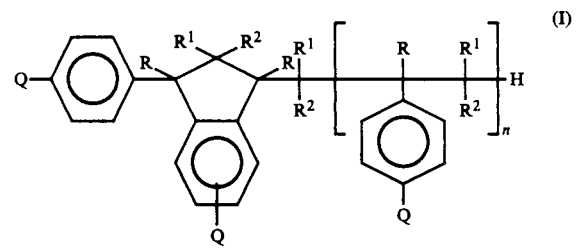

In the preferred compositions the quantity of compound/compounds of formula (I) is between 0.5 and 5% w/w of the composition.

The compounds (I) are incorporated into the composition by simply dissolving them therein at ambient temperature.

The photochemical crosslinking of the photopolymerisable compositions is effected, as is normal in this sector, by irradiation with mercury vapour lamps having emission spectra of between 250 and 550.

As far as is known to the applicant, the compounds of formula (I) are new and have not been previously described in the literature.

According to one characteristic of the invention the products of formula (I) are prepared from a compound of styrene type by a series of reactions which cause it to undergo cyclisation with simultaneous oligomerisation, followed by the introduction of carbonyl groups, and in particular alphaketo-ester, halo-ketone and alphahydroxy-ketone groups, into the molecules.

Compounds of styrene type particularly useful as raw materials in the production of compounds (I) include styrene, alpha-methylstyrene, styrene substituted in alpha with $C_2$–$C_4$ alkyls and diphenylethylene.

The cyclisation and oligomerisation of compounds of styrene type is widely described in the literature.

According to a basic characteristic of the present invention, the cyclisation and oligomerisation of the styrene compounds is effected simultaneously by controlling the reaction temperature at between −10° and 150° C. for a time of between 0.5 and 8 hours in the presence of an acid catalyst but in the absence of solvent to obtain a mixture of cyclised and non-cyclised dimers and trimers of the starting compound.

The preferred acid catalysts are acid clays, ion exchange resins with sulphonic groups in acid form, $C_1-C_{18}$ alkyl acids and $C_6-C_{18}$ aryl-sulphonic acids, of which those in insoluble solid form are particularly preferred because of their ease of separation from the reaction mixtures on termination of the reaction.

The dimer:trimer molar ratio is between 30:70 and 70:30 and the cyclised:non-cyclised compound molar ratio is between 10:90 and 90:10.

The reaction mixture can be distilled to separate the individual components in their pure state. In the preferred embodiment of the invention the reaction mixture is simply treated to remove the catalyst, generally by filtration, and is then subjected as such to the subsequent functionalisation reactions to introduce the carbonyl groups into the molecules of the various components of the mixture.

Whether the hydrocarbon mixture as such from the cyclisation reaction or the individual components in pure form are reacted, the reaction for introducing carbonyl groups into the molecule, and in particular alphaketo-ester, haloketone or alphahydroxyketone groups, is effected as described in the preceding European patent application No. 161463 of the present applicant.

EXAMPLE 1

Preparation of 1,1,3-trimethyl-1-phenylindan

A solution of 6.13 g of methanesulphonic acid in 57.14 g of alphamethylstyrene is heated to 80° C. at which an exothermic reaction commences and raises the mass temperature to 160° C. On termination of the exothermic reaction, the mass is cooled to 100° C. and this temperature is maintained while 400 g of alphamethylstyrene are added over a period of 2 hours. The mixture is cooled and filtered through absorbent earth to obtain 450 g of practically colourless product which solidifies on cooling. It has the following characteristics:

M.P.: 48°-51° C.; IR spectrum (cm$^{-1}$): 2950, 1600, 1480, 1445, 1030, 760, 700, 540; NMR spectrum: (CDCl$_3$, δ, ppm) 1.05 (s, 3H); 1.37 (s, 3H); 1.72 (s, 3H); 2.2 (d, 1H, J=13 Hz); 2.5 (d, 1H, J=13 Hz); 7.1-7.4 (m, 9H). The confirmed structure for the compound obtained is:

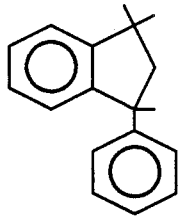

corresponding to 1,3,3-trimethyl-1-phenylindan (Ia)

EXAMPLE 2

Reaction of Ia with isobutyryl chloride to obtain the isobutyl diketone derivative (Ib) of 1,3,3-trimethyl-1-phenylindan A solution of 230.5 g of product Ia (obtained as in Example 1) in 515 g of methylenedichloride containing 218 g of isobutyryl chloride is cooled to 0° C. and treated with 274 g of anhydrous aluminium chloride.

Two hours after termination of the addition, the mixture is hydrolysed with 1 liter of water at 5°-10° C. The aqueous phase is separated and the organic phase washed with water until neutral, after which the solvent is removed by evaporation. 350 g of ketone are obtained as intermediate for the subsequent functionalisation.

IR spectrum (cm$^{-1}$): 2970, 1683, 1605, 1470, 1230, 973, 850.

EXAMPLE 3

Chlorination of Ib to obtain the relative chloroketone (Ic)

310 g of sulphuryl chloride are added to a solution of 350 g of ketone Ib (obtained as in the preceding example) in 380 g of toluene while maintaining the temperature at 40° C. After 3 hours of reaction, the mixture is treated with 500 g of water at 15°-20° C.

The aqueous phase is removed and the organic phase washed repeatedly until neutral. The solution thus obtained can be used directly as intermediate in the subsequent substitution reaction

EXAMPLE 4

The chloroketone, useful as a photoinitiator, is isolated by cooling the toluene solution to 0°-5° C. and filtering off the solid obtained after crystallisation. It is dried to obtain 175 g of product having the following characteristics:

M.P.: 138°-139° C.; TLC (eluent toluene): single elongated spot; IR spectrum (cm$^{-1}$): 2970, 1670, 1605, 1460, 1445, 1390, 1370, 1275, 1170, 1120, 985, 850, 770, 750, 700;

NMR: (CDCl$_3$, δ, ppm): 1.05 (s, 3H); 1.38 (s, 3H); 1.74 (s, 3H); 1.87 (s, 6H); 1.90 (2s, 3H), 2.2-2.5 (q, 2H, J=13.2 Hz); 7.2-7.3, 7.9-8.19 (m, 7H).

Elementary analysis. Theoretical for $C_{26}H_{30}O_2Cl_2$: C=70.11, H=6.79, Cl=15.91; Found: C=70.83, H=7.09, Cl=16.04.

The structure of the obtained compound, confirmed by IR and NMR spectrum and by microanalysis, is the following:

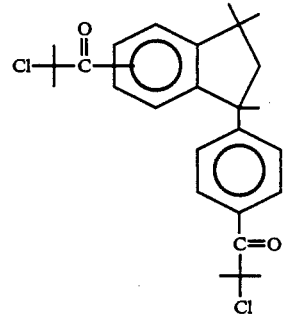

The NMR analysis showing the aromatic proton multiplet indicates that in crystallisation there is enrichment with isomer which places the chloroketone residue in position 5 on the indan nucleus.

EXAMPLE 4

Preparation of alpha hydroxyisopropylketone (I)

The toluene solution obtained in Example 3 is treated with 80 ml of methanol and 367 g of a 30% w/w solution of sodium methylate in methanol, while maintaining the temperature below 30° C. On termination, the mixture is treated with 200 ml of water and then with 225 g of 37% hydrochloric acid. The aqueous phase is then removed and the organic phase washed repeatedly with water until neutral.

On termination, the toluene is evaporated under a 1 mmHg vacuum at 60° C. to obtain 346 g of product, which on cooling becomes a vitreous solid with the following characteristics:

Pour point: 40°-50° C.

IR spectrum (cm$^{-1}$): 3460, 2960, 1675, 1605, 1465, 1370, 1270, 1170, 915, 840, 775, 755, 730, 715, 697, 590, 565, 530.

NMR spectrum: (CDCl$_3$, δ, ppm): 0.999 (s, 3H); 1.32 (s, 3H); 1.51 (s, 6H); 1.55 (2s, 6H), 1.68 (s, 3H), 2.18-2.47 (q, 2H, J=13.3 Hz); 4.28 (Br, OH), 7.09/7.27-7.82/8.04 (m, 7H).

Elementary analysis for $C_{26}H_{32}O_4$: theoretical: C=76.46, H=7.90; found: C=76.20, H=8.20.

The structure of the obtained compound, confirmed by IR and NMR spectra and by microanalysis, is the following:

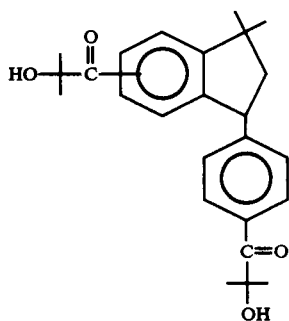

The NMR analysis showing the aromatic proton multiplet indicates the presence of isomers carrying the alphahydroxyketone group in position 5 or 6 of the indan nucleus.

High pressure liquid chromatographic analysis (HPLC) (eluent MeOH/H$_2$O 70:30, column 2×RP18 5 m×10 cm, 260 nm UV detector) shows that the weight ratio of isomers in position 5 to isomers in position 6 is about 70:30.

EXAMPLE 5

The reaction of Example 4 is repeated but using the alpha chloroketone (175 g) isolated as crystalline solid in Example 3 (reaction solvent toluene). On termination an alpha hydroxyketone (160 g) is obtained with analytical characteristics identical to those of Example 4 but with an Ir spectrum with resolved aromatic multiplet indicating the following structure:

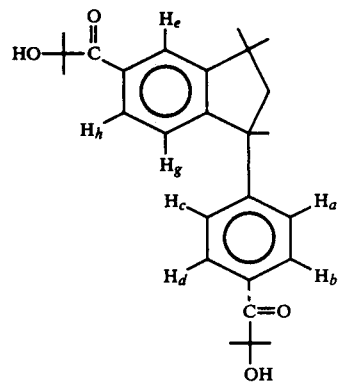

| (ppm) | 7.2016–7.2441 | (d, 2H(a,c)), | J = 8.5 Hz |
| | 7.2273–7.2669 | (d, 1H(g)), | J = 8.06 Hz |
| | 7.8226–7.8293 | (d, 1H(e)), | J = 1.5 Hz |
| | 7.9055–7.9485 | (d, 2H(d,b)), | J = 8.5 Hz |
| | 7.9939–8.0016 | (dd, 1H(h)), | J = 1.5 Hz |
| | 8.0341–8.0419 | | J = 8.06 Hz |

The example shows that the isomer of the hydroxyketone compound with the substituent in position 5 of the indan nucleus can be isolated in pure form.

EXAMPLE 6

Purification of the compound obtained in Example 4

The compound obtained in Example 4 can be further purified by crystallisation, by dissolving the reaction product in toluene (60% w/w solution) at 60°-70° C. and allowing the hydroxyketone to crystallise.

By cooling and filtration, a white solid is obtained which is washed on the filter with a toluene-hexane (1:5) mixture and dried. In this manner a crystalline solid is obtained having a M.P. of 120°-123° C. and the following IR spectrum (KBr) (cm$^{-1}$): 3430, 3360, 2980, 2960, 2860, 1685, 1660, 1600, 1465, 1410, 1325, 1270, 1250, 1175, 1145, 1045, 1015, 1005, 990, 965, 860, 840, 830, 775, 755, 720, 640, 570.

If the spectrum is recorded for the molten product it is identical to that of the product of Example 4, showing that the difference is due to the high crystallinity of the analysed product in KBr.

EXAMPLE 7

The reaction of Example 4 is repeated using the residual alpha chloroketone (175 g) from the mother liquor of crystallisation of Example 3. On termination, an alphahydroxyketone is obtained, which is taken up in toluene at 60° C. to give a 60% w/w solution. The obtained solid is filtered off through a Buchner funnel and washed with a toluene-hexane (1:5) mixture and dried, to obtain 80 g of a crystalline white solid with analytical characteristics identical to those of the compound obtained in Example 5. In particular, the NMR (CDCl$_3$) spectrum shows a resolved aromatic multiplet indicative of the following structure:

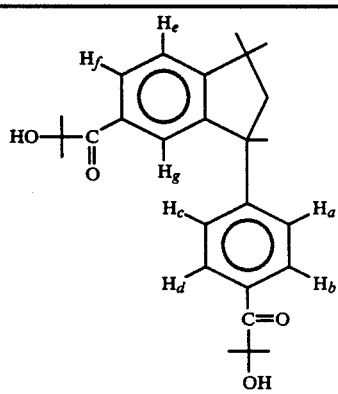

| (ppm) | 7.1624–7.2025 | (d, 1H(e), | J = 8.02 Hz) |
|---|---|---|---|
| | 7.2406–7.2646 | (d, 2H(a,c), | J = 8.36 Hz) |
| | 7.8907–7.8989 | (d, 1H(g), | J = 1.65 Hz) |
| | 7.9192–7.9611 | (d, 2H(d,b), | J = 8.36 Hz) |
| | 7.9376–7.9493 | (dd, 1H(f), | J = 1.65 Hz) |
| | 7.9776–7.9861 | | J = 8.02 Hz) |

The example shows that the isomer of the hydroxyketone compound with the substituent in position 6 of the indan nucleus can be isolated in pure form.

EXAMPLE 8

Reaction of Ia with ethyloxalyl chloride to obtain the relative alphaketoester

A solution of 173.7 g of 1,3,3-trimethyl-phenylindan (Ia, Ex. 1) in 400 g of methylene chloride and 210.5 g of ethyloxalyl chloride is treated at 0°–5° C. with 209.7 g of anhydrous aluminium chloride.

On termination, the mixture is hydrolysed in 1 liter of water and ice. The aqueous phase is removed and the organic phase is washed repeatedly with water until neutral. The solvent is then evaporated at 1 mmHg and 60° C. to obtain 205 g of a viscous liquid with the following characteristics:

appearance: light yellow viscous liquid

IR spectrum (cm$^{-1}$): 2960, 2930, 2860, 1790, 1683, 1605, 1450, 1370, 1320, 1305, 1210, 1190, 1100, 1025, 840, 765, 700.

The IR spectrum, the preparation reaction and analogy with the syntheses described heretofore indicate the following structure:

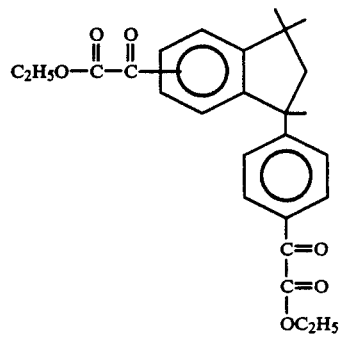

EXAMPLE 9

Preparation of alphahydroxyketone

A sample of 1,2-dimethyl-1-phenyl-3-(2-methyl-2-phenylpropyl)indan (obtained by separation using vacuum distillation at 135° C., 1 mmHg from a mixture with 1,3,3-trimethyl-phenylindan) was subjected to the sequence of reactions indicated in Examples 2, 3 and 4 to obtain the alphahydroxyketone (If) with the following characteristics:

appearance: light yellow viscous liquid

IR spectrum (cm$^{-1}$): 3470, 2970, 1675, 1603, 1465, 1380, 1365, 1260, 1170, 1067, 1010, 970, 840, 770, 755, 730, 700.

NMR spectrum: (CDCl$_3$, δ, ppm): 1.06–1.098 (2s, 3H); 1.39–1.40 (2s, 3H); 1.62 (s, 12H); 1.68–1.69 (2s, 6H), 1.65–1.66 (2s, 3H), 1.71–1.73 (2s, 3H), 2.2–2.5 (q, 2H, J=13.2 Hz); 2.36 (s, 2H), 7.16/7.28–7.92/7.96 (m, 11H).

Elementary analysis for C$_{39}$H$_{48}$O$_6$: theoretical: C=76.44, H=7.89; found: C=76.65, H=8.04.

The IR and NMR spectra, elementary analysis and analogy with the aforegoing syntheses indicate the following structure:

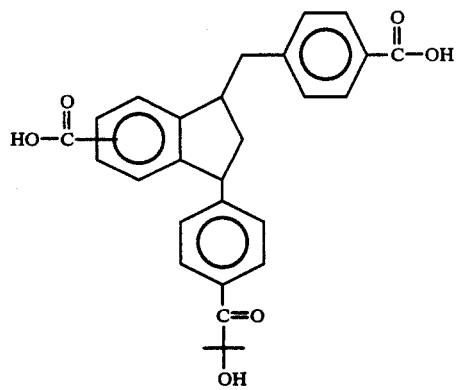

The NMR spectrum analysis indicates that the compound consists of a mixture of isomers with the hydroxyketone substituent in positions 5 and 6 of the indan nucleus respectively.

EXAMPLE 10

Mixture of hydroxyketone compounds with photoinitiator activity, resulting from the multistage preparation process (a) Preparation of a mixture of 2,3-dihydro-1,1,3-trimethyl-3-phenyl-1H-indene (A) and 2,3-dihydro-1,3-dimethyl-1-(2-methyl-2-phenyl)propyl-3-phenyl-1H-indene (B).

10 g of alphamethylstyrene are mixed with 3 g of Amberlist 15 (sulphonated polystyrene resin in acid form by Rohm and Haas) and heated under agitation to 100° C. A further 90 g of alphamethylstyrene are then added over 1 hour while maintaining the temperature at 100° C. On termination, the resin is removed by filtration and the obtained liquid is cooled to obtain 97 g of product with the following analytical characteristics:

| appearance: | colourless crystalline solid |
|---|---|
| melting point: | 43–46° C. |
| infrared spectrum: | identical to that of Example 1 |
| HPLC analysis: | 80% compound A |
| | 20% compound B |

(b) Functionalisation The mixture obtained under point (a) is subjected to acylation with isobutyryl chloride under the conditions of Example 2.

The reaction product is subjected to chlorination under the conditions of Example 3.

The reaction product is subjected to the reaction conditions of Example 4 to obtain a mixture of compounds (a+b of Example 4 and a+b of Example 9) in the form of a high viscosity liquid with a pour point of between 40° and 50° C.

IR spectrum (cm$^{-1}$): 3460, 2960, 1675, 1605, 1465, 1375, 1275, 1170, 920, 830, 770, 750, 710, 690, 585, 525.

NMR spectrum: (CDCl$_3$, δ, ppm): 0.99–1.1 (b, CH$_3$-C), 1.32–1.40 (b, CH$_3$C), 1.50–1.73 (b, Ch$_3$-COH+CH$_3$C), 2.2–2.5 (q, CH$_2$), 2.36 (s, CH$_2$), 7.1–8.04 (m, ArH)

EXAMPLE 11

To evaluate the characteristics of the carbonyl derivatives of 1-phenylindan according to the invention, the following resin formulations were used (all parts are by weight):

| A. | Polyurethane acrylate: | |
| --- | --- | --- |
| | Photomer 6250 (contains 25% of tripropyleneglycoldiacrylate) | 90 |
| | N-vinylpyrrolidone | 10 |
| | Photoinitiator as stated in the tables | |
| B. | Polyester acrylate: | |
| | Photomer 5029 | 100 |
| | Photoinitiator as stated in the tables | |
| C. | Water-dilutable acrylate resin: | |
| | Lankro RCP 1789 | 90 |
| | Water | 10 |
| | Photoinitiator | 3 |
| D. | Aqueous emulsion of photo-crosslinkable polyester acrylate resin: | |
| | Laromer PE 55 W (50% dry substance) | 100 |
| | Photoinitiator as stated in the tables | |

Photomer is a Lamsko trademark
Laromer is a BASF trademark

TABLE 1

Evaluation of polymerisation rate:
The mixtures A and B are spread on cardboard to a thickness of 50 μm and crosslinked by a Hanovia 6512-A-431 lamp at 80 W/cm at 10 cm distance. The evaluation criterion is the maximum speed (in m/min) at which the film is no longer tacky

| | PHOTOINITIATOR (parts by wt.) | | | | | | | |
| --- | --- | --- | --- | --- | --- | --- | --- | --- |
| | 1 | | 2 | | 3 | | 4 | |
| FORMULATION | A | B | A | B | A | B | A | B |
| PIMP[1] | 3.5 | 2 | 7.5 | 3 | 17.0 | 4 | 24.0 | 6 |
| prod. Ex 4 | 3.5 | 3 | 11.5 | 4 | 30.0 | 7 | 80.0 | 20 |
| prod. Ex 5 | 4.0 | 3 | 28 | 5 | 61.0 | 14.0 | 80.0 | 45 |
| prod. Ex 6 | 4.0 | 3 | 27.0 | 5 | 60.0 | 13.5 | 80.0 | 45 |
| prod. Ex 9 | 3.5 | 3 | 12.0 | 4.5 | 30.0 | 7.5 | 65.0 | 25 |
| prod. Ex 8 | 3.5 | 4 | 10.0 | 10 | 30.0 | — | 30.0 | — |
| prod. Ex 10 | 3.5 | 3 | 11.0 | 4 | 30.0 | 7 | 80.0 | 25 |
| prod. Ex 3 | | | 3.0 | 2 | 6.0 | 3 | | |

[1] Poly-2-hydroxy-2-methyl-p-(1-methylvinyl)propiophenone Ex. 2, EP Application 161463

The data indicate that the indan compounds of hydroxyketone and glyoxyl type have better activity than those cited in EP No. 161463. In the case of chloroketone, some activity is noted but not at the level of the other compounds.

TABLE 2

Evaluation of crosslinked film hardness.
The mixtures A and B are spread on glass to a thickness of 100 μm and crosslinked under the conditions of Table 1 at two different speeds: A at 10 m/min and B at 2 m/min.
The hardness was evaluated in accordance with DIN 53157 (Koenig pendulum, in seconds).

| | PHOTOINITIATOR (parts by wt.) | | | | | | | |
| --- | --- | --- | --- | --- | --- | --- | --- | --- |
| | 1 | | 2 | | 3 | | 4 | |
| FORMULATION | A | B | A | B | A | B | A | B |
| PIMP | 54 | 98 | 94 | 121 | 132 | 125 | 100 | 119 |
| prod. Ex 4 | 58 | 124 | 153 | 143 | 163 | 135 | 152 | 137 |
| prod. Ex 5 | 59 | 124 | 152 | 135 | 164 | 134 | 167 | 130 |
| prod. Ex 6 | 59 | 120 | 152 | 131 | 164 | 133 | 176 | 126 |
| prod. Ex 9 | 58 | 122 | 151 | 135 | 162 | 135 | 158 | 130 |
| prod. Ex 8 | 30 | 86 | 23 | 120 | 17 | 125 | 30 | — |
| prod. Ex 10 | 55 | 120 | 140 | 140 | 160 | 135 | 150 | 135 |
| prod. Ex 3 | — | — | 65 | 46 | 72 | 53 | — | — |
| HCPK[2] | — | — | 94 | 116 | 131 | 120 | — | — |

[2] hydroxycyclohexylphenylketone (known photoinitiator used in the art)

The data indicate that the indan and hydroxyketone compounds have a higher activity than PIMP and HCPK.

The derivatives of glyoxyl and chloroketone type however also have a high level of photoinitiator activity.

Evaluation of thermal stability:

All formulations based on mixtures A and B exceed 30 days at 60° C. in darkness in a closed environment.

TABLE 3

Evaluation of colour after crosslinking.
The mixtures A and B are spread on cardboard to a thickness of 100 μm and crosslinked under the conditions indicated in Table 1. The colour index (YI) is measured by instruments in accordance with ASTM D 1925.

| | PHOTOINITIATOR (parts by wt.) | | | | | | | |
| --- | --- | --- | --- | --- | --- | --- | --- | --- |
| | 1 | | 2 | | 3 | | 4 | |
| FORMULATION | A | B | A | B | A | B | A | B |
| PIMP | 12.85 | 15.12 | 12.53 | 16.87 | 13.45 | 17.59 | 14.10 | 16.70 |
| prod. Ex 4 | 12.09 | 15.03 | 12.49 | 16.17 | 13.0 | 15.92 | 13.41 | 17.85 |
| prod. Ex 5 | 12.00 | 15.10 | 12.20 | 15.50 | 12.35 | 15.65 | 12.5 | 16.20 |
| prod. Ex 6 | 12.02 | 15.91 | 12.48 | 15.60 | 12.46 | 15.88 | 12.6 | 16.30 |
| prod. Ex 9 | 12.05 | 15.00 | 12.5 | 15.9 | 12.6 | 16.1 | 12.8 | 16.2 |
| prod. Ex 8 | 12.74 | 14.00 | 12.40 | 14.57 | 13.30 | — | 14.3 | — |
| prod. Ex 10 | 12.10 | 15.10 | 12.50 | 16.00 | 13.00 | 15.9 | 13.4 | — |

TABLE 4

Evaluation of resistance to ageing.
The formulations A and B containing 3% of photoinitiator are applied and crosslinked as in Table 1 and the resultant films are subjected to accelerated ageing in a weatherometer. The yellow index (YI) is evaluated in accordance with ASTM D 1925 at different ageing times.

| FORMULATION | B | | | | A | | |
| --- | --- | --- | --- | --- | --- | --- | --- |
| DAYS | 2 | 4 | 6 | 8 | 7 | 14 | 21 |
| PHOTOINIT: | | | | | | | |
| PIMP | 24 | 29 | 31 | 34 | 18.5 | 20.0 | 21.0 |
| Prod. Ex 6 | 22 | 27 | 29 | 31 | 16.5 | 17.3 | 18.0 |
| BDK[3] | 25 | 31 | 34 | 38 | 20.5 | 22.0 | 23.5 |

[3] Benzyldimethylketal (a known photoinitiator used in the art)

The data indicate that the indan compounds have excellent resistance to ageing under photo-oxidative conditions compared with PIMP and BDK.

TABLE 5

Evaluation of odour after photopolymerisation.
Formulation C is spread on glass to a thickness of 100 μm
and the resultant film crosslinked with a 6512-A-431 Hanovia lamp
at 80 w/cm at 10 cm distance at a speed of 5 m/min.
The resultant films are immediately subjected to organoleptic
examination to test the residual odour.

| PHOTOINITIATOR | ODOUR |
| --- | --- |
| PIMP | absent |
| prod. EX. 4 | " |
| prod. EX. 5 | " |
| prod. EX. 6 | " |
| prod. EX. 8 | " |
| prod. EX. | " |
| prod. EX. 3 | " |
| HCPK | intense and pungent[5] |
| HIPK[4] | intense and pungent[5] |

[4]hydroxypropylphenylketone (known photoinitiator used in the art)
[5]benzaldehyde odour The data indicate that neither the indan compounds nor PIMP give rise to intense odour (of benzaldehyde) during photolysis of the various photoinitiators under the actual conditions used, in contrast to HCPK and HIPK.

TABLE 6

Evaluation of photoinitiator volatility.
The photoinitiator samples are heated to 100° C. in an oven
under natural air circulation. The weight loss (% of initial
material) is evaluated as a function of time.

| PHOTOINITIATOR | 500 | 1000 | 2000 min. |
| --- | --- | --- | --- |
| PIMP | 0.5 | 1 | 3 |
| prod. Ex. 4 | 0.2 | 0.8 | 2.5 |
| prod. Ex. 5 | 0.15 | 0.5 | 0.6 |
| prod. Ex. 6 | 0.15 | 0.5 | 0.6 |
| prod. Ex. 9 | 0.2 | 0.7 | 0.9 |
| HCPK | 5 | 10 | 25 |
| HIPK | 45 | 60 | 82 |

The data indicate low volatility for all indan compounds.

TABLE 7

Evaluation of activity in photo-crosslinkable emulsion.
Formulation D is applied to glass to a wet thickness of 100 μm
and dried in an oven at 110° C. under forced ventilation for
various times. The dry films are crosslinked by exposure to a
.6512 A 431 Hanovia UV lamp at 80 W/cm at a distance of 10
cm and a speed of 10 m/min.
Hardness is measured in accordance with DIN 53157 (Koenig
pendulum in seconds).

| PHOTOINITIATOR (parts/wt) | 2 | | | 4 | | |
| --- | --- | --- | --- | --- | --- | --- |
| DRYING TIME (min) | 2 | 5 | 10 | 2 | 5 | 10 |
| PIMP | 55 | 55 | 55 | 70 | 70 | 70 |
| prod. Ex 4 | 60 | 60 | 60 | 75 | 75 | 75 |
| HIPK | 46 | 20 | 0 | 45 | 25 | 0 |
| HIDPK[6] | 42 | 42 | 42 | 50 | 50 | 50 |

[6]hydroxy isopropyl-p-dodecylphenylketone (known photoinitiator)

The data indicate that the indan compounds are considerably better than HIPK and HIDPK and also better than PIMP.

We claim:

1. A process for the photopolymerisation of compounds containing ethylenic double bonds, using as photoinitiator agent one or more carbonyl derivatives of 1-phenylindan having the following general formula:

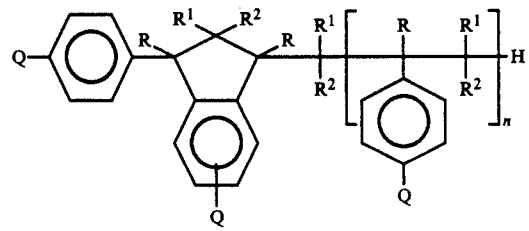

where:
n: ranges from 0 to 1
R, $R^1$, $R^2$: which are identical or different, each independently represent H, $C_1$–$C_3$ alkyl
Q: represents a

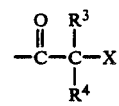

group in which
$R^3$, $R^4$, which are identical or different independently represent:
$C_1$–$C_8$ alkyl
together represent a $C_3$–$C_7$ polyalkylene group
together are coincident in an oxygen atom
X: is Cl, OH, or OR in which R has the aforesaid meaning.

2. A process as claimed in claim 1, wherein the photoinitiator agent is a mixture of:
    (a) 2,3-dihydro-5-(2-methyl-1-oxopropyl)-1,1,3-trimethyl-3-[4-(2-methyl-1-oxopropyl)phenyl]-1H-indene;
    (b) 2,3-dihydro-6-(2-methyl-1-oxopropyl)-1,1,3-trimethyl-3-[4-(2-methyl-1-oxopropyl)phenyl]-1H-indene.

3. A process as claimed in claim 1, wherein the photoinitiator agent is a mixture of:
    (a) 2,3-dihydro-5-(2-chloro-2-methyl-1-oxopropyl)-1,1,3-trimethyl-3-[4-(2-chloro-2-methyl-1-oxopropyl)phenyl]-1H-indene;
    (b) 2,3-dihydro-6-(2-chloro-2-methyl-1-oxopropyl)-1,1,3-trimethyl-3-[4-(2-chloro-2-methyl-1-oxopropyl)phenyl]-1H-indene.

4. A process as claimed in claim 1, wherein the photoinitiator agent is a mixture of:
    (a) 2,3-dihydro-5-(2-hydroxy-2-methyl-1-oxopropyl)-1,1,3-trimethyl-3-[4-(2-hydroxy-2-methyl-1-oxopropyl)phenyl]-1H-indene;
    (b) 2,3-dihydro-6-(2-hydroxy-2-methyl-1-oxopropyl)-1,1,3-trimethyl-3-[4-(2-hydroxy-2-methyl-1-oxopropyl)phenyl]-1H-indene.

5. A process as claimed in claim 1, wherein the photoinitiator agent is:
2,3-dihydro-5-(2-hydroxy-2-methyl-1-oxopropyl)-1,1,3-trimethyl-3-[4-(2-hydroxy-2-methyl-1-oxopropyl)phenyl]-1H-indene.

6. A process as claimed in claim 1, wherein the photoinitiator agent is:
2,3-dihydro-6-(2-hydroxy-2-methyl-1-oxopropyl)-1,1,3-trimethyl-3-[4-(2-hydroxy-2-methyl-1-oxopropyl)phenyl]-1H-indene.

7. A process as claimed in claim 1, wherein the photoinitiator agent is:

2,3-dihydro-6-(2-hydroxy-2-methyl-1-oxopropyl)-1,1,3-trimethyl-3-[4-(2-hydroxy-2-methyl-1-oxopropyl)phenyl]-1H-indene.

8. A process as claimed in claim 1, wherein the photoinitiator agent is a mixture of:
(a) 2,3-dihydro-5-(2-ethoxy-1,2-dioxoethyl)-1,1,3-trimethyl-3-[4-(2-ethoxy-1,2-dioxoethyl)phenyl]-1H-indene;
(b) 2,3-dihydro-6-(2-ethoxy-1,2-dioxoethyl)-1,1,3-trimethyl-3-[4-(2-ethoxy-1,2-dioxoethyl)phenyl]-1H-indene.

9. A process as claimed in claim 1, wherein the photoinitiator agent is a mixture of:
(a) 2,3-dihydro-1,3-dimethyl-5-(2-hydroxy-2-methyl-1-oxopropyl)-1-{2-methyl-2-[4-(2-hydroxy-2-methyl-1-oxopropyl)phenyl]propyl}-3-[4-(2-hydroxy-2-methyl-1-oxopropyl)phenyl]-1H-indene;
(b) 2,3-dihydro-1,3-dimethyl-6-(2-hydroxy-2-methyl-1-oxopropyl)-1-{2-methyl-2-[4-(2-hydroxy-2-methyl-1-oxopropyl)phenyl]propyl}-3-[4-(2-hydroxy-2-methyl-1-oxopropyl)phenyl]-1H-indene.

10. A compound of general formula:

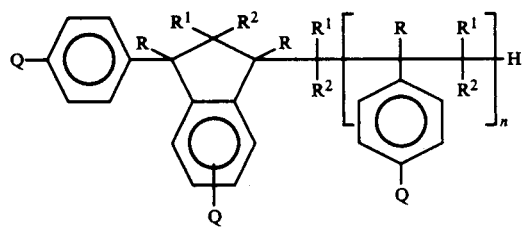

where:
n: ranges from 0 to 1
R, R$^1$, R$^2$: which are identical or different, each independently represent H, C$_1$-C$_3$ alkyl
Q: represents a

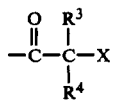

group in which R$^3$, R$^4$, which are identical or different, independently represent:
C$_1$-C$_8$ alkyl
together represent a C$_3$-C$_7$ polyalkylene group
together are coincident in an oxygen atom
X: is Cl, OH, or OR in which R has the aforesaid meaning,
having the property of acting as a photosensitive agent in the radical polymerisation of compounds with ethylenic double bonds to which it is added in an effective quantity.

11. A photopolymerisable composition comprising compounds or mixtures of compounds with olefinic double bonds and at least one compound of general formula:

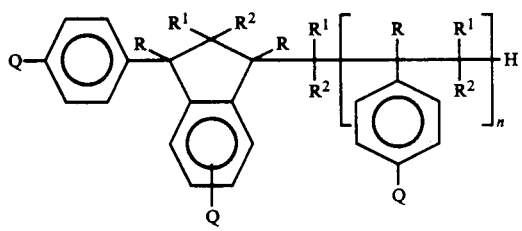

where:
n: ranges from 0 to 1
R, R$^1$, R$^2$: which are identical or different, each independently represent H, C$_1$-C$_3$ alkyl
Q: represents a

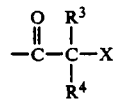

group in which R$^3$, R$^4$, which are identical or different independently represent:
C$_1$-C$_8$ alkyl
together represent a C$_3$-C$_7$ polyalkylene group
together are coincident in an oxygen atom
X: is Cl, OH, or OR in which R has the aforesaid meaning,
in a quantity of between 0.1 and 10 parts by weight per 100 parts of composition.

12. A process for preparing carbonyl derivatives of 1-phenylindan, or a mixture thereof, having the following general formula:

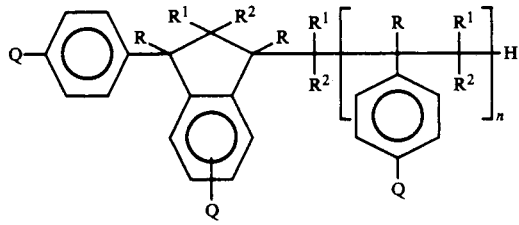

where:
n: ranges from 0 to 1
R, R$^1$, R$^2$: which are identical or different, each independently represent H, C$_1$-C$_3$ alkyl
Q: represents a

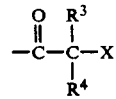

group in which R$^3$, R$^4$, which are identical or different independently represent:
C$_1$-C$_8$ alkyl
together represent a C$_3$-C$_7$ polyalkylene group
together are coincident in an oxygen atom
X: is Cl, OH, or OR in which R has the aforesaid meaning,
consisting of:
heating a compound of styrene type to a temperature of between −10° C. and 150° C. for a time of between 0.5 and 8 hours in the presence of an acid catalyst but in the absence of solvent;
separating the acid catalyst from the reaction mixture;
then treating in known manner said reaction mixture containing compounds with a 1-phenylindan structure to convert them into the desired carbonyl derivatives.

13. A process as claimed in claim 12, wherein the acid catalyst is an acid clay or an ion exchange resin with sulphonic groups in acid form or alkylsulphonic acids or arylsulphonic acids.

14. A process as claimed in claim 12, wherein the catalyst is in solid form.

* * * * *